US011986590B2

(12) United States Patent
Christensen et al.

(10) Patent No.: US 11,986,590 B2
(45) Date of Patent: May 21, 2024

(54) VAPORIZER WICKING ELEMENTS INCLUDING A HOLLOW CORE

(71) Applicant: JUUL Labs, Inc., San Francisco, CA (US)

(72) Inventors: Steven Christensen, San Mateo, CA (US); Alexander J. Gould, Portola Valley, CA (US); Esteban Leon Duque, San Francisco, CA (US)

(73) Assignee: JUUL LABS, INC., San Francisco, CA (US)

( * ) Notice: Subject to any disclaimer, the term of this patent is extended or adjusted under 35 U.S.C. 154(b) by 1069 days.

(21) Appl. No.: 16/453,953

(22) Filed: Jun. 26, 2019

(65) Prior Publication Data

US 2019/0387797 A1  Dec. 26, 2019

Related U.S. Application Data

(60) Provisional application No. 62/690,315, filed on Jun. 26, 2018.

(51) Int. Cl.
| | | |
|---|---|---|
| *A24F 13/00* | (2006.01) | |
| *A24B 15/167* | (2020.01) | |
| *A24F 40/44* | (2020.01) | |
| *A61M 15/06* | (2006.01) | |
| *H05B 3/44* | (2006.01) | |
| *A24F 40/10* | (2020.01) | |

(52) U.S. Cl.
CPC .......... *A61M 15/06* (2013.01); *A24B 15/167* (2016.11); *A24F 40/44* (2020.01); *H05B 3/44* (2013.01); *A24F 40/10* (2020.01)

(58) Field of Classification Search
CPC ....................................................... A24F 47/00
USPC .................................................. 131/328–329
See application file for complete search history.

(56) References Cited

U.S. PATENT DOCUMENTS

| | | | |
|---|---|---|---|
| 5,303,720 | A | 4/1994 | Banerjee et al. |
| 6,155,268 | A | 12/2000 | Takeuchi |
| 6,598,607 | B2 | 4/2003 | Adiga et al. |
| 6,909,840 | B2 | 6/2005 | Harwig et al. |

(Continued)

FOREIGN PATENT DOCUMENTS

| | | |
|---|---|---|
| CA | 2868914 C | 10/2013 |
| CA | 2935072 C | 5/2018 |

(Continued)

OTHER PUBLICATIONS

U.S. Appl. No. 15/855,890, filed Dec. 27, 2017, U.S. Pat. No. 11,129,414.

(Continued)

*Primary Examiner* — Phuong K Dinh
(74) *Attorney, Agent, or Firm* — Mintz, Levin, Cohn, Ferris, Glovsky and Popeo, P.C.

(57) ABSTRACT

A vaporization device is described that includes a cartridge having a wicking element that can efficiently and effectively draw vaporizable material contained in a reservoir of the cartridge to a heating element for vaporizing the vaporizable material. In some embodiments, the wicking element includes a hollow core or a thermally conductive core surrounded by a porous wicking material. Various embodiments of the wicking element are described, as well as related systems, methods, and articles of manufacture.

28 Claims, 9 Drawing Sheets

(56) References Cited

U.S. PATENT DOCUMENTS

| | | |
|---|---|---|
| 7,726,320 B2 | 6/2010 | Robinson et al. |
| 7,793,861 B2 | 9/2010 | Bankers et al. |
| 8,678,012 B2 | 3/2014 | Li et al. |
| 8,910,640 B2 | 7/2014 | Sears et al. |
| 8,857,446 B2 | 10/2014 | Wu |
| 9,010,335 B1 | 4/2015 | Scatterday |
| 9,072,321 B2 | 7/2015 | Liu |
| 9,204,670 B2 | 12/2015 | Liu |
| 9,220,303 B2 | 12/2015 | Li et al. |
| 9,320,300 B2 | 4/2016 | Hon |
| 9,386,805 B2 | 7/2016 | Liu |
| 9,427,026 B2 | 8/2016 | Wu |
| 9,456,632 B2 | 10/2016 | Hon |
| 9,456,633 B2 | 10/2016 | Liu |
| 9,497,997 B2 | 11/2016 | Wu |
| 9,504,279 B2 | 11/2016 | Chen |
| 9,510,624 B2 | 12/2016 | Li et al. |
| 9,526,272 B2 | 12/2016 | Liu |
| 9,603,390 B2 | 3/2017 | Li et al. |
| 9,609,893 B2 | 4/2017 | Novak et al. |
| 9,648,909 B2 | 5/2017 | Zhou et al. |
| 9,675,117 B2 | 6/2017 | Li et al. |
| 9,675,118 B2 | 6/2017 | Chen |
| 9,730,471 B2 | 8/2017 | Li et al. |
| 9,861,130 B2 | 1/2018 | Li et al. |
| 9,943,108 B2 | 4/2018 | Lord |
| 9,986,761 B2 | 6/2018 | Thorens et al. |
| 9,986,762 B2 | 6/2018 | Alarcon et al. |
| 9,999,250 B2 | 6/2018 | Minskoff et al. |
| 10,070,668 B2 | 9/2018 | Li et al. |
| 10,111,466 B2 | 10/2018 | Lord |
| 10,131,532 B2 | 11/2018 | Murison et al. |
| 10,136,675 B2 | 11/2018 | Li et al. |
| 10,285,444 B2 | 5/2019 | Clemens et al. |
| 2008/0056691 A1 | 3/2008 | Wingo et al. |
| 2010/0065653 A1 | 3/2010 | Wingo et al. |
| 2013/0104916 A1 | 5/2013 | Bellinger et al. |
| 2013/0192618 A1 | 8/2013 | Li et al. |
| 2013/0192623 A1 | 8/2013 | Tucker et al. |
| 2013/0213419 A1 | 8/2013 | Tucker et al. |
| 2013/0255702 A1 | 10/2013 | Griffith, Jr. et al. |
| 2013/0284192 A1 | 10/2013 | Peleg |
| 2013/0306064 A1 | 11/2013 | Thorens et al. |
| 2014/0000638 A1 | 1/2014 | Sebastian |
| 2014/0069424 A1 | 3/2014 | Poston et al. |
| 2014/0109898 A1 | 4/2014 | Li et al. |
| 2014/0109921 A1 | 4/2014 | Chen |
| 2014/0130817 A1 | 5/2014 | Li et al. |
| 2014/0150785 A1 | 6/2014 | Malik et al. |
| 2014/0182612 A1 | 7/2014 | Chen |
| 2014/0196733 A1 | 7/2014 | Liu |
| 2014/0209105 A1 | 7/2014 | Sears et al. |
| 2014/0209108 A1 | 7/2014 | Li et al. |
| 2014/0261487 A1 | 9/2014 | Chapman et al. |
| 2014/0261488 A1 | 9/2014 | Tucker |
| 2014/0299137 A1 | 10/2014 | Kieckbusch et al. |
| 2014/0332022 A1 | 11/2014 | Li et al. |
| 2015/0007836 A1 | 1/2015 | Li et al. |
| 2015/0027455 A1 | 1/2015 | Peleg et al. |
| 2015/0040929 A1 | 2/2015 | Hon |
| 2015/0164146 A1 | 6/2015 | Li et al. |
| 2015/0181943 A1 | 7/2015 | Li et al. |
| 2015/0181944 A1 | 7/2015 | Li et al. |
| 2015/0201674 A1 | 7/2015 | Dooly et al. |
| 2015/0208728 A1 | 7/2015 | Lord |
| 2015/0208729 A1 | 7/2015 | Monsees et al. |
| 2015/0217068 A1 | 8/2015 | Wakalopulos |
| 2015/0237916 A1 | 8/2015 | Farine et al. |
| 2015/0282529 A1 | 10/2015 | Li et al. |
| 2015/0296886 A1 | 10/2015 | Li et al. |
| 2015/0296887 A1* | 10/2015 | Zhu ............... A24F 40/485 131/329 |
| 2015/0305406 A1 | 10/2015 | Li et al. |
| 2015/0305407 A1 | 10/2015 | Li et al. |
| 2015/0305408 A1 | 10/2015 | Liu |
| 2015/0357839 A1 | 12/2015 | Cai et al. |
| 2015/0374035 A1 | 12/2015 | Sanchez et al. |
| 2016/0000147 A1 | 1/2016 | Li et al. |
| 2016/0007655 A1 | 1/2016 | Li et al. |
| 2016/0044964 A1 | 2/2016 | Liu |
| 2016/0044966 A1 | 2/2016 | Li et al. |
| 2016/0057811 A1 | 2/2016 | Alarcon et al. |
| 2016/0073693 A1 | 3/2016 | Reevell |
| 2016/0106155 A1 | 4/2016 | Reevell |
| 2016/0113326 A1 | 4/2016 | Li et al. |
| 2016/0128390 A1 | 5/2016 | Liu |
| 2016/0135505 A1* | 5/2016 | Li ............... H05B 3/46 131/329 |
| 2016/0135506 A1 | 5/2016 | Sanchez et al. |
| 2016/0143360 A1 | 5/2016 | Sanchez et al. |
| 2016/0150828 A1 | 6/2016 | Goldstein et al. |
| 2016/0157523 A1 | 6/2016 | Liu |
| 2016/0174611 A1 | 6/2016 | Monsees et al. |
| 2016/0183596 A1 | 6/2016 | Rado |
| 2016/0192707 A1 | 7/2016 | Li et al. |
| 2016/0219938 A1 | 8/2016 | Mamoun et al. |
| 2016/0255876 A1 | 9/2016 | Rostami |
| 2016/0262453 A1 | 9/2016 | Ampolini et al. |
| 2016/0295915 A1 | 10/2016 | Jochnowitz et al. |
| 2016/0309786 A1 | 10/2016 | Holtz |
| 2016/0331035 A1 | 11/2016 | Cameron |
| 2016/0334119 A1 | 11/2016 | Cameron |
| 2016/0341419 A1 | 11/2016 | Fluhrer |
| 2016/0360790 A1 | 12/2016 | Calfee et al. |
| 2017/0006916 A1 | 1/2017 | Liu |
| 2017/0006917 A1 | 1/2017 | Alvarez |
| 2017/0027223 A1 | 2/2017 | Eksouzian |
| 2017/0027232 A1 | 2/2017 | Scheck et al. |
| 2017/0043106 A1 | 2/2017 | Hyland et al. |
| 2017/0043910 A1 | 2/2017 | Hopps et al. |
| 2017/0045150 A1 | 2/2017 | Marsh |
| 2017/0045994 A1 | 2/2017 | Murison et al. |
| 2017/0056883 A1 | 3/2017 | Aarts et al. |
| 2017/0099878 A1 | 4/2017 | Murison et al. |
| 2017/0105453 A1 | 4/2017 | Li et al. |
| 2017/0105454 A1 | 4/2017 | Li et al. |
| 2017/0112193 A1 | 4/2017 | Chen |
| 2017/0127723 A1 | 5/2017 | Wu |
| 2017/0135399 A1 | 5/2017 | Gavrielov et al. |
| 2017/0156399 A1 | 6/2017 | Freeman et al. |
| 2017/0196263 A1 | 7/2017 | Sur |
| 2017/0208868 A1 | 7/2017 | Li et al. |
| 2017/0215481 A1 | 8/2017 | Li et al. |
| 2017/0224017 A1 | 8/2017 | Li et al. |
| 2017/0224018 A1 | 8/2017 | Li et al. |
| 2017/0231276 A1 | 8/2017 | Mironov et al. |
| 2017/0231282 A1 | 8/2017 | Bowen et al. |
| 2017/0231286 A1 | 8/2017 | Borkovec et al. |
| 2017/0233114 A1 | 8/2017 | Christensen et al. |
| 2017/0238617 A1 | 8/2017 | Scatterday |
| 2017/0259170 A1 | 9/2017 | Bowen et al. |
| 2017/0273360 A1 | 9/2017 | Brinkley et al. |
| 2017/0280779 A1 | 10/2017 | Qiu |
| 2017/0340018 A1 | 11/2017 | Thorens |
| 2017/0367402 A1 | 12/2017 | Lau et al. |
| 2017/0367407 A1 | 12/2017 | Althorpe et al. |
| 2018/0007972 A1* | 1/2018 | Thorens ............... A61M 11/003 |
| 2018/0027877 A1 | 2/2018 | Tucker et al. |
| 2018/0027879 A1 | 2/2018 | Gavrielov et al. |
| 2018/0035713 A1 | 2/2018 | Macko et al. |
| 2018/0037381 A1 | 2/2018 | White et al. |
| 2018/0043115 A1 | 2/2018 | Gould et al. |
| 2018/0064169 A1 | 3/2018 | Biel et al. |
| 2018/0077967 A1 | 3/2018 | Hatton et al. |
| 2018/0098575 A1 | 4/2018 | Liu |
| 2018/0098576 A1 | 4/2018 | Hedarchet |
| 2018/0110263 A1 | 4/2018 | Borkovec et al. |
| 2018/0116292 A1 | 5/2018 | Atkins et al. |
| 2018/0146711 A1 | 5/2018 | Mazur et al. |
| 2018/0160735 A1 | 6/2018 | Borkovec et al. |
| 2018/0160737 A1 | 6/2018 | Verleur et al. |
| 2018/0162769 A1 | 6/2018 | Peuchert et al. |
| 2018/0168227 A1 | 6/2018 | Fraser et al. |
| 2018/0177240 A1 | 6/2018 | Duque et al. |

(56) References Cited

U.S. PATENT DOCUMENTS

| | | | |
|---|---|---|---|
| 2018/0184722 A1 | 7/2018 | Murison et al. |
| 2018/0220707 A1 | 8/2018 | Biel et al. |
| 2018/0279679 A1 | 10/2018 | Mcadam et al. |
| 2018/0296777 A1 | 10/2018 | Terry et al. |
| 2019/0246693 A1 | 8/2019 | Nettenstrom et al. |
| 2019/0373953 A1 | 12/2019 | Atkins et al. |
| 2020/0107585 A1 | 4/2020 | Atkins et al. |
| 2020/0128874 A1 | 4/2020 | Atkins et al. |
| 2020/0221771 A1 | 7/2020 | Atkins et al. |
| 2020/0275696 A1 | 9/2020 | Atkins et al. |

FOREIGN PATENT DOCUMENTS

| | | | |
|---|---|---|---|
| CN | 101228969 A | 7/2008 |
| CN | 201375023 Y | 1/2010 |
| CN | 101862038 A | 10/2010 |
| CN | 103338664 B | 10/2013 |
| CN | 203234036 U | 10/2013 |
| CN | 103859604 A | 6/2014 |
| CN | 103859604 B | 6/2014 |
| CN | 104010529 B | 8/2014 |
| CN | 203986105 U | 12/2014 |
| CN | 204132390 U | 2/2015 |
| CN | 104540404 A | 4/2015 |
| CN | 204317492 U | 5/2015 |
| CN | 104684422 A | 6/2015 |
| CN | 105011375 A | 11/2015 |
| CN | 105188428 A | 12/2015 |
| CN | 105208882 A | 12/2015 |
| CN | 105208882 B | 12/2015 |
| CN | 105357995 A | 2/2016 |
| CN | 105394816 A | 3/2016 |
| CN | 105473012 A | 4/2016 |
| CN | 205695698 U | 11/2016 |
| CN | 106686996 B | 5/2017 |
| CN | 207285198 U | 5/2018 |
| CN | 108697175 B | 10/2018 |
| CN | 209090052 U | 7/2019 |
| EP | 2404515 A1 | 1/2012 |
| EP | 2614731 A1 | 7/2013 |
| EP | 2925395 A1 | 10/2015 |
| EP | 2928330 B1 | 10/2015 |
| EP | 3020292 A1 | 5/2016 |
| EP | 3072407 A1 | 9/2016 |
| EP | 3078281 A1 | 10/2016 |
| EP | 3200559 | * 2/2017 |
| EP | 3170414 A1 | 5/2017 |
| EP | 3292773 A1 | 3/2018 |
| EP | 3562535 B1 | 11/2019 |
| GB | 2504076 A | 1/2014 |
| GB | 2513637 A | 11/2014 |
| GB | 201511359 | 8/2015 |
| JP | 2012506263 A | 3/2012 |
| JP | 2015500025 A | 1/2015 |
| JP | 2015509718 A | 4/2015 |
| JP | 2015524258 A | 8/2015 |
| JP | 2015198985 A | 11/2015 |
| JP | 2017127649 A | 7/2017 |
| JP | 2018509158 A | 4/2018 |
| KR | 200461404 Y1 | 7/2012 |
| KR | 20130092252 A | 8/2013 |
| KR | 101554435 B1 | 9/2015 |
| KR | 101691984 B1 | 9/2016 |
| TW | 201438608 A | 10/2014 |
| WO | WO-2011146174 A2 | 11/2011 |
| WO | WO-2013060781 A1 | 5/2013 |
| WO | WO-2014101734 A1 | 7/2014 |
| WO | WO-2014130692 A1 | 8/2014 |
| WO | WO-2014150979 A2 | 9/2014 |
| WO | WO-2015107552 A1 | 7/2015 |
| WO | WO-2015109476 A1 | 7/2015 |
| WO | WO-2016023181 A1 | 2/2016 |
| WO | WO-2016023182 A1 | 2/2016 |
| WO | WO-2016023183 A1 | 2/2016 |
| WO | WO-2016023809 A1 | 2/2016 |
| WO | WO-2016054793 A1 | 4/2016 |
| WO | WO-2016079155 A1 | 5/2016 |
| WO | WO-2016145072 A1 | 9/2016 |
| WO | WO-2016187943 A1 | 12/2016 |
| WO | WO-2016202033 A1 | 12/2016 |
| WO | WO-2017001352 A2 | 1/2017 |
| WO | WO-2017036829 A1 | 3/2017 |
| WO | WO-2017054424 A1 | 4/2017 |
| WO | WO-2017072284 A1 | 5/2017 |
| WO | WO-2017093535 A1 | 6/2017 |
| WO | WO-2017176111 A1 | 10/2017 |
| WO | WO-2017207419 A1 | 12/2017 |
| WO | WO-2017207443 A1 | 12/2017 |
| WO | WO-2018078546 A2 | 5/2018 |
| WO | WO-2020081849 A2 | 4/2020 |

OTHER PUBLICATIONS

U.S. Appl. No. 17/481,119, filed Sep. 21, 2021.
U.S. Appl. No. 17/483,569, filed Sep. 23, 2021.
International Search Report issued for International Patent Application No. PCT/US2017/068577, mailed on Apr. 23, 2018, 5 pages.

* cited by examiner

Aerosol Out

200

206

205

204

203

+  −

202  220

Air in
201

FIG. 3

VAPORIZER WICKING ELEMENTS INCLUDING A HOLLOW CORE

CROSS-REFERENCE TO RELATED APPLICATION

This application claims priority to U.S. Provisional Application No. 62/690,315, filed on Jun. 26, 2018, and titled "VAPORIZER WICKING ELEMENTS," the entirety of which is incorporated by reference herein.

TECHNICAL FIELD

The subject matter described herein relates to vaporizer devices, including various embodiments of a wick for assisting with vaporizing vaporizable material.

BACKGROUND

Electronic vaporizers typically use an atomizer system that includes a wicking element with a resistive heating element. During use of a vaporizer device, the user inhales an aerosol, commonly called vapor, which may be generated by the heating element that vaporizes (e.g., causing a liquid or solid to at least partially transition to the gas phase) a vaporizable material. The vaporizable material used with a vaporizer can be provided within a cartridge.

Some cartridges include a wicking element that may serve at least two purposes: to draw liquid from the reservoir to the atomizer where it can be vaporized by the heating element, and to allow air to enter the reservoir to replace at least some of the volume of liquid removed. For example, when a user inhales or puffs on the vaporizer, the heating element may be activated. Additionally, air drawn into the vaporizer as a result of the puff may pass over the saturated wick and heating element, thereby allowing the passing air to collect vapor that may condense and enter the user's lungs. During and/or after the puff, capillary action of the wick may pull more liquid from the reservoir into the wick and at least some air may enter the reservoir through the wick to replace the volume of fluid drawn out of the reservoir.

SUMMARY

Aspects of the current subject matter relate to wicking elements, such as various embodiments of thermal and hollow wicks for use in a vaporizer device. Thermal and hollow wick configurations consistent with implementations described herein may provide benefits, such as for example by enhancing performance of a vaporizer device in vaporizing a vaporizable material.

In one aspect, a cartridge for a vaporization device includes a reservoir configured to hold a vaporizable material, a wick that is configured to draw the vaporizable material from the reservoir to a vaporization region, and a heating element. The wick includes a porous wicking material surrounding at least a part of a hollow core. The heating element is disposed within the vaporization region and adjacent the wick and is configured to heat the vaporizable material drawn from the reservoir.

In another aspect, a wick is configured to be included in a cartridge for use in a vaporization device. The wick includes a porous wicking material surrounding at least a portion of a hollow core and a support structure configured to retain a shape of the hollow core.

In some variations, one or more of the following features may optionally be included in any feasible combination. The hollow core of the wick may be in fluid communication with the reservoir. The hollow core of the wick may be configured to extend between opposing ends of the wick. The opposing ends of the wick may each include an opening that allows the vaporizable material to flow into the hollow core. The support structure may include a spring having a helical shape. The shape of the hollow core may include a cylindrical shape. The porous wicking material may allow one or more of a radially directed absorption of the vaporizable material and/or an axially directed absorption of the vaporizable material. The hollow core may be void of material and/or the vaporizable material may be a liquid. The hollow core may include a thermally conductive material extending therethrough. The heating element may be a coil that wraps around a circumference of the wick. The heating element may be in thermal communication with the wick thereby allowing the heating element to increase a temperature of at least the porous wicking material.

In another interrelated aspect of the current subject matter, a method includes drawing a vaporizable material along a wick in a first direction. The wick includes a porous wicking material surrounding at least a portion of a hollow core. The method also includes drawing the vaporizable material along the wick in a second direction, which is orthogonal to the first direction and which extends between the hollow core and an outer surface of the porous wicking material. In some variations, the first direction may extend parallel to a longitudinal axis of the wick. The method may further include transferring heat along a thermally conductive material extending along the hollow core.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings:

FIG. 3 illustrates a schematic representation of a vaporizer cartridge including a wick;

DETAILED DESCRIPTION

Figure 1A:
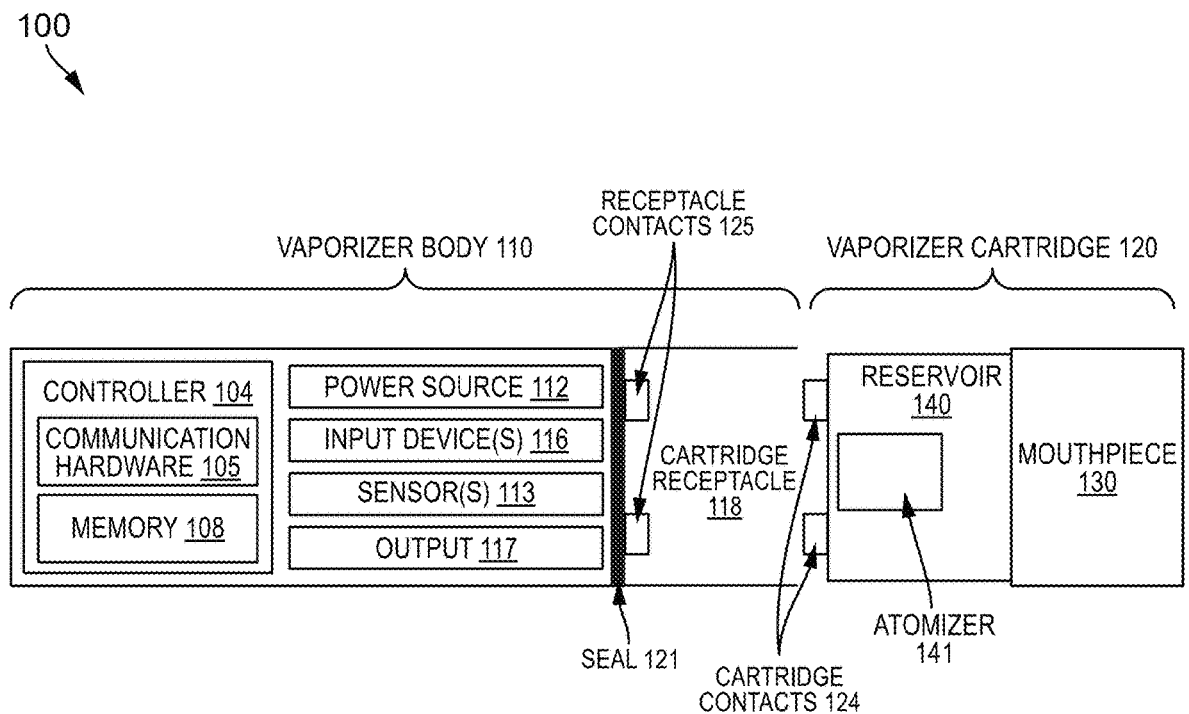
FIG. 1A illustrates a block diagram illustrating features of a vaporizer device having a vaporizer cartridge and a vaporizer device body, consistent with implementations of the current subject matter.

The disclosure provided herein is directed to vaporizer devices, including vaporizers configured to couple with vaporizer cartridges containing one or more vaporizable materials for vaporization and inhalation by a user. The term "vaporizer" is used generically in the following description to refer to a vaporizer device. Examples of vaporizers consistent with implementations of the current subject matter include electronic vaporizers or the like. Such vaporizers are generally portable, hand-held devices that heat a vaporizable material to provide an inhalable dose of the material.

The vaporizable material used with a vaporizer may optionally be provided within a cartridge (e.g., a part of the vaporizer that contains the vaporizable material in a reservoir or other container and that can be refillable when empty or disposable in favor of a new cartridge containing additional vaporizable material of a same or different type). A vaporizer may be a cartridge-using vaporizer, a cartridge-less vaporizer, or a multi-use vaporizer capable of use with or without a cartridge. For example, a multi-use vaporizer may include a heating chamber (e.g., an oven) configured to receive a vaporizable material directly in the heating chamber and also to receive a cartridge or other replaceable device having a reservoir, a volume, or the like for at least partially containing a usable amount of vaporizable material.

In various implementations, a vaporizer may be configured for use with liquid vaporizable material (e.g., a carrier solution in which an active and/or inactive ingredient(s) are suspended or held in solution or a neat liquid form of the vaporizable material itself) or a solid vaporizable material.

Some currently available cartridges include a wick configured to draw vaporizable material from the reservoir to the atomizer. Wicks used in currently available vaporizers may be formed by bundling together fine, continuous filaments of silica glass or cotton fibers to form a cord or rope, and may be characterized by a nominal outer diameter, number of threads, and/or a linear density. For example, such wicks can have a capillary flow rate (a rate at which liquid is drawn into and along the length of the wick) that results in inefficient and ineffective use and vaporization of the vaporizable material. For example, during use of a vaporizer device having such a wick, the vaporizable material may not be replenished along the wick fast enough to allow for subsequent puffs from the vaporizer device to result in sufficient or desired amounts of vaporized material for inhalation. Furthermore, as the viscosity of the vaporizable material increases, the capillary flow rate can be further decreased, thereby further negatively affecting the amount of vaporizable material that is able to be vaporized during subsequent puffs from the vaporizer. High-viscosity solutions (e.g., vaporizable oils) may also reduce the rate at which air can return to the reservoir (e.g., via the wick), which may even further reduce the capillary flow rate.

Implementations of the current subject matter include various embodiments of a wick that may be included in a vaporizer cartridge for improving the efficiency and effectiveness of vaporizing at least one vaporizable material contained within one or more reservoirs of the vaporizer cartridge. For example, some implementations of the wick described herein include a hollow fluid chamber or passageway (referred to herein as a "hollow wick"). The fluid chamber or passageway of the hollow wick can assist with shortening the flow path through the wick thereby increasing the rate at which vaporizable fluid can be transferred from the reservoir to the vaporization chamber, as will be described in greater detail below.

Additionally, some implementations of the wick described herein include one or more thermally conductive materials (referred to herein as a "thermal wick"). Such thermally conductive materials may increase thermal conductivity capabilities of the thermal wick, such as compared to wicks used in currently available vaporizers. This may allow a greater length of the thermal wick to reach a higher temperature more quickly, which may lower the viscosity of vaporizable fluid in the thermal wick and adjacent reservoir. Such lowered viscosity may allow increased capillary action along the thermal wick. The increase in capillary action may also assist with allowing air to travel through the thermal wick more efficiently and effectively for relieving a pressure drop in the reservoir due to vaporizable fluid being drawn out of the reservoir (e.g., by capillary action of the wick and subsequent vaporization by a heating element). The thermal wick may also distribute excess temperature gradients along the thermal wick, thereby reducing or eliminating hot spots and cold spots that can be common in wicks used in currently available vaporizers. Additionally, the thermal wick may have a decreased heat-up time compared to wicks used in currently available vaporizers. Various embodiments of the thermal wick are described in greater detail below.

Referring to the block diagram of FIG. 1A, a vaporizer 100 typically includes a power source 112 (such as a battery which may be a rechargeable battery), and a controller 104 (e.g., a processor, circuitry, etc. capable of executing logic) for controlling delivery of heat to an atomizer 141 to cause a vaporizable material to be converted from a condensed form (e.g., a solid, a liquid, a solution, a suspension, a part of an at least partially unprocessed plant material, etc.) to the gas phase. The controller 104 may be part of one or more printed circuit boards (PCBs) consistent with certain implementations of the current subject matter.

After conversion of the vaporizable material to the gas phase, and depending on the type of vaporizer, the physical and chemical properties of the vaporizable material, and/or other factors, at least some of the gas-phase vaporizable material may condense to form particulate matter in at least a partial local equilibrium with the gas phase as part of an aerosol, which can form some or all of an inhalable dose provided by the vaporizer 100 for a given puff or draw on the vaporizer. It will be understood that the interplay between gas and condensed phases in an aerosol generated by a vaporizer can be complex and dynamic, as factors such as ambient temperature, relative humidity, chemistry, flow conditions in airflow paths (both inside the vaporizer and in the airways of a human or other animal), mixing of the gas-phase or aerosol-phase vaporizable material with other air streams, etc. may affect one or more physical parameters of an aerosol. In some vaporizers, and particularly for vaporizers for delivery of more volatile vaporizable materials, the inhalable dose may exist predominantly in the gas phase (i.e., formation of condensed phase particles may be very limited).

Vaporizers for use with liquid vaporizable materials (e.g., neat liquids, suspensions, solutions, mixtures, etc.) typically include an atomizer 141 in which a wicking element (also referred to herein as a wick) conveys an amount of a liquid vaporizable material to a part of the atomizer that includes a heating element. The wicking element is generally configured to draw liquid vaporizable material from a reservoir configured to contain (and that may in use contain) the liquid vaporizable material such that the liquid vaporizable material may be vaporized by heat delivered from a heating element. The wicking element may also optionally allow air to enter the reservoir to replace the volume of liquid removed. In other words, capillary action pulls liquid vaporizable material into the wick for vaporization by the heating element (described herein), and air may, in some implementations of the current subject matter, return to the reservoir through the wick to at least partially equalize pressure in the reservoir. Other approaches to allowing air back into the reservoir to equalize pressure are also within the scope of the current subject matter.

The heating element can be or include one or more of a conductive heater, a radiative heater, and a convective heater. One type of heating element is a resistive heating element, which can be constructed of or at least include a material (e.g., a metal or alloy, for example a nickel-chromium alloy, or a non-metallic resistor) configured to dissipate electrical power in the form of heat when electrical current is passed through one or more resistive segments of the heating element. In some implementations of the current subject matter, an atomizer can include a heating element that includes resistive coil or other heating element wrapped around, positioned within, integrated into a bulk shape of, pressed into thermal contact with, or otherwise arranged to deliver heat to a wicking element to cause a liquid vaporizable material drawn by the wicking element from a reservoir to be vaporized for subsequent inhalation by a user in a gas and/or a condensed (e.g., aerosol particles or droplets) phase. Other wicking element, heating element, and/or atomizer assembly configurations are also possible, as discussed further below.

Certain vaporizers may also or alternatively be configured to create an inhalable dose of gas-phase and/or aerosol-phase vaporizable material via heating of a non-liquid vaporizable material, such as for example a solid-phase vaporizable material (e.g., a wax or the like) or plant material (e.g., tobacco leaves and/or parts of tobacco leaves) containing the vaporizable material. In such vaporizers, a resistive heating element may be part of or otherwise incorporated into or in thermal contact with the walls of an oven or other heating chamber into which the non-liquid vaporizable material is placed. Alternatively, a resistive heating element or elements may be used to heat air passing through or past the non-liquid vaporizable material to cause convective heating of the non-liquid vaporizable material. In still other examples, a resistive heating element or elements may be disposed in intimate contact with plant material such that direct conductive heating of the plant material occurs from within a mass of the plant material (e.g., as opposed to only by conduction inward form walls of an oven).

The heating element may be activated (e.g., a controller, which is optionally part of a vaporizer body as discussed below, may cause current to pass from the power source through a circuit including the resistive heating element, which is optionally part of a vaporizer cartridge as discussed below), in association with a user puffing (e.g., drawing, inhaling, etc.) on a mouthpiece 130 of the vaporizer to cause air to flow from an air inlet, along an airflow path that passes an atomizer (e.g., wicking element and heating element), optionally through one or more condensation areas or chambers, to an air outlet in the mouthpiece. Incoming air passing along the airflow path passes over, through, etc. the atomizer, where gas phase vaporizable material is entrained into the air. As noted above, the entrained gas-phase vaporizable material may condense as it passes through the remainder of the airflow path such that an inhalable dose of the vaporizable material in an aerosol form can be delivered from the air outlet (e.g., in a mouthpiece 130 for inhalation by a user).

Activation of the heating element may be caused by automatic detection of the puff based on one or more of signals generated by one or more sensors 113, such as for example a pressure sensor or sensors disposed to detect pressure along the airflow path relative to ambient pressure (or optionally to measure changes in absolute pressure), one or more motion sensors of the vaporizer, one or more flow sensors of the vaporizer, a capacitive lip sensor of the vaporizer; in response to detection of interaction of a user with one or more input devices 116 (e.g., buttons or other tactile control devices of the vaporizer 100), receipt of signals from a computing device in communication with the vaporizer; and/or via other approaches for determining that a puff is occurring or imminent.

As alluded to in the previous paragraph, a vaporizer consistent with implementations of the current subject matter may be configured to connect (e.g., wirelessly or via a wired connection) to a computing device (or optionally two or more devices) in communication with the vaporizer. To this end, the controller 104 may include communication hardware 105. The controller 104 may also include a memory 108. A computing device can be a component of a vaporizer system that also includes the vaporizer 100, and can include its own communication hardware, which can establish a wireless communication channel with the communication hardware 105 of the vaporizer 100. For example, a computing device used as part of a vaporizer system may include a general-purpose computing device (e.g., a smartphone, a tablet, a personal computer, some other portable device such as a smartwatch, or the like) that executes software to produce a user interface for enabling a user of the device to interact with a vaporizer. In other implementations of the current subject matter, such a device used as part of a vaporizer system can be a dedicated piece of hardware such as a remote control or other wireless or wired device having one or more physical or soft (e.g., configurable on a screen or other display device and selectable via user interaction with a touch-sensitive screen or some other input device like a mouse, pointer, trackball, cursor buttons, or the like) interface controls. The vaporizer can also include one or more output 117 features or devices for providing information to the user.

A computing device that is part of a vaporizer system as defined above can be used for any of one or more functions, such as controlling dosing (e.g., dose monitoring, dose setting, dose limiting, user tracking, etc.), controlling sessioning (e.g., session monitoring, session setting, session limiting, user tracking, etc.), controlling nicotine delivery (e.g., switching between nicotine and non-nicotine vaporizable material, adjusting an amount of nicotine delivered, etc.), obtaining locational information (e.g., location of other users, retailer/commercial venue locations, vaping locations, relative or absolute location of the vaporizer itself, etc.), vaporizer personalization (e.g., naming the vaporizer, locking/password protecting the vaporizer, adjusting one or more parental controls, associating the vaporizer with a user group, registering the vaporizer with a manufacturer or warranty maintenance organization, etc.), engaging in social activities (e.g., games, social media communications, interacting with one or more groups, etc.) with other users, or the like. The terms "sessioning", "session", "vaporizer session," or "vapor session," are used generically to refer to a period devoted to the use of the vaporizer. The period can include a time period, a number of doses, an amount of vaporizable material, and/or the like.

In the example in which a computing device provides signals related to activation of the resistive heating element, or in other examples of coupling of a computing device with a vaporizer for implementation of various control or other functions, the computing device executes one or more computer instructions sets to provide a user interface and underlying data handling. In one example, detection by the computing device of user interaction with one or more user interface elements can cause the computing device to signal the vaporizer 100 to activate the heating element, either to a full operating temperature for creation of an inhalable dose of vapor/aerosol. Other functions of the vaporizer may be controlled by interaction of a user with a user interface on a computing device in communication with the vaporizer.

The temperature of a resistive heating element of a vaporizer may depend on a number of factors, including an amount of electrical power delivered to the resistive heating element and/or a duty cycle at which the electrical power is delivered, conductive heat transfer to other parts of the electronic vaporizer and/or to the environment, latent heat losses due to vaporization of a vaporizable material from the wicking element and/or the atomizer as a whole, and convective heat losses due to airflow (e.g., air moving across the heating element or the atomizer as a whole when a user inhales on the electronic vaporizer). As noted above, to reliably activate the heating element or heat the heating element to a desired temperature, a vaporizer may, in some implementations of the current subject matter, make use of signals from a pressure sensor to determine when a user is inhaling. The pressure sensor can be positioned in the airflow path and/or can be connected (e.g., by a passageway or other path) to an airflow path connecting an inlet for air to enter the device and an outlet via which the user inhales the resulting vapor and/or aerosol such that the pressure sensor experiences pressure changes concurrently with air passing through the vaporizer device from the air inlet to the air outlet. In some implementations of the current subject matter, the heating element may be activated in association with a user's puff, for example by automatic detection of the puff, for example by the pressure sensor detecting a pressure change in the airflow path.

Typically, the pressure sensor (as well as any other sensors 113) can be positioned on or coupled (e.g., electrically or electronically connected, either physically or via a wireless connection) to the controller 104 (e.g., a printed circuit board assembly or other type of circuit board). To take measurements accurately and maintain durability of the vaporizer, it can be beneficial to provide a resilient seal 121 to separate an airflow path from other parts of the vaporizer. The seal 121, which can be a gasket, may be configured to at least partially surround the pressure sensor such that connections of the pressure sensor to internal circuitry of the vaporizer are separated from a part of the pressure sensor exposed to the airflow path. In an example of a cartridge-based vaporizer, the seal 121 may also separate parts of one or more electrical connections between a vaporizer body 110 and a vaporizer cartridge 120. Such arrangements of a seal 121 in a vaporizer 100 can be helpful in mitigating against potentially disruptive impacts on vaporizer components resulting from interactions with environmental factors such as water in the vapor or liquid phases, other fluids such as the vaporizable material, etc. and/or to reduce escape of air from the designed airflow path in the vaporizer. Unwanted air, liquid or other fluid passing and/or contacting circuitry of the vaporizer can cause various unwanted effects, such as alter pressure readings, and/or can result in the buildup of unwanted material, such as moisture, the vaporizable material, etc. in parts of the vaporizer where they may result in poor pressure signal, degradation of the pressure sensor or other components, and/or a shorter life of the vaporizer. Leaks in the seal 121 can also result in a user inhaling air that has passed over parts of the vaporizer device containing or constructed of materials that may not be desirable to be inhaled.

A general class of vaporizers that have recently gained popularity includes a vaporizer body 110 that includes a controller 104, a power source 112 (e.g., battery), one more sensors 113, charging contacts, a seal 121, and a cartridge receptacle 118 configured to receive a vaporizer cartridge 120 for coupling with the vaporizer body through one or more of a variety of attachment structures. In some examples, vaporizer cartridge 120 includes a reservoir 140 for containing a liquid vaporizable material and a mouthpiece 130 for delivering an inhalable dose to a user. The vaporizer cartridge can include an atomizer 141 having a wicking element and a heating element, or alternatively, one or both of the wicking element and the heating element can be part of the vaporizer body. In implementations in which any part of the atomizer 141 (e.g., heating element and/or wicking element) is part of the vaporizer body, the vaporizer can be configured to supply liquid vaporizer material from a reservoir in the vaporizer cartridge to the atomizer part(s) included in the vaporizer body.

Cartridge-based configurations for vaporizers that generate an inhalable dose of a non-liquid vaporizable material via heating of a non-liquid vaporizable material are also within the scope of the current subject matter. For example, a vaporizer cartridge may include a mass of a plant material that is processed and formed to have direct contact with parts of one or more resistive heating elements, and such a vaporizer cartridge may be configured to be coupled mechanically and electrically to a vaporizer body the includes a processor, a power source, and electrical contacts for connecting to corresponding cartridge contacts for completing a circuit with the one or more resistive heating elements.

In vaporizers in which the power source 112 is part of a vaporizer body 110 and a heating element is disposed in a vaporizer cartridge 120 configured to couple with the vaporizer body 110, the vaporizer 100 may include electrical connection features (e.g., means for completing a circuit) for completing a circuit that includes the controller 104 (e.g., a printed circuit board, a microcontroller, or the like), the power source, and the heating element. These features may include at least two contacts on a bottom surface of the vaporizer cartridge 120 (referred to herein as cartridge contacts 124) and at least two contacts disposed near a base of the cartridge receptacle (referred to herein as receptacle contacts 125) of the vaporizer 100 such that the cartridge contacts 124 and the receptacle contacts 125 make electrical connections when the vaporizer cartridge 120 is inserted into and coupled with the cartridge receptacle 118. The circuit completed by these electrical connections can allow delivery of electrical current to the resistive heating element and may further be used for additional functions, such as for example for measuring a resistance of the resistive heating element for use in determining and/or controlling a temperature of the resistive heating element based on a thermal coefficient of resistivity of the resistive heating element, for identifying a cartridge based on one or more electrical characteristics of a resistive heating element or the other circuitry of the vaporizer cartridge, etc.

In some examples of the current subject matter, the at least two cartridge contacts and the at least two receptacle contacts can be configured to electrically connect in either of at least two orientations. In other words, one or more circuits necessary for operation of the vaporizer can be completed by insertion of a vaporizer cartridge 120 in the cartridge receptacle 118 in a first rotational orientation (around an axis along which the end of the vaporizer cartridge having the cartridge is inserted into the cartridge receptacle 118 of the vaporizer body 110) such that a first cartridge contact of the at least two cartridge contacts 124 is electrically connected to a first receptacle contact of the at least two receptacle contacts 125 and a second cartridge contact of the at least two cartridge contacts 124 is electrically connected to a second receptacle contact of the at least two receptacle contacts 125. Furthermore, the one or more circuits necessary for operation of the vaporizer can be completed by insertion of a vaporizer cartridge 120 in the cartridge receptacle 118 in a second rotational orientation such that the first cartridge contact of the at least two cartridge contacts 124 is electrically connected to the second receptacle contact of the at least two receptacle contacts 125 and the second cartridge contact of the at least two cartridge contacts 124 is electrically connected to the first receptacle contact of the at least two receptacle contacts 125. This feature of a vaporizer cartridge 120 being reversible insertable into a cartridge receptacle 118 of the vaporizer body 110 is described further below.

In one example of an attachment structure for coupling a vaporizer cartridge 120 to a vaporizer body, the vaporizer body 110 includes a detent (e.g., a dimple, protrusion, etc.) protruding inwardly from an inner surface the cartridge receptacle 118. One or more exterior surfaces of the vaporizer cartridge 120 can include corresponding recesses (not shown in FIG. 1A) that can fit and/or otherwise snap over such detents when an end of the vaporizer cartridge 120 inserted into the cartridge receptacle 118 on the vaporizer body 110. When the vaporizer cartridge 120 and the vaporizer body 110 are coupled (e.g., by insertion of an end of the vaporizer cartridge 120 into the cartridge receptacle 118 of the vaporizer body 110), the detent into the vaporizer body 110 may fit within and/or otherwise be held within the recesses of the vaporizer cartridge 120 to hold the vaporizer cartridge 120 in place when assembled. Such a detent-recess assembly can provide enough support to hold the vaporizer cartridge 120 in place to ensure good contact between the at least two cartridge contacts 124 and the at least two receptacle contacts 125, while allowing release of the vaporizer cartridge 120 from the vaporizer body 110 when a user pulls with reasonable force on the vaporizer cartridge 120 to disengage the vaporizer cartridge 120 from the cartridge receptacle 118.

Further to the discussion above about the electrical connections between a vaporizer cartridge and a vaporizer body being reversible such that at least two rotational orientations of the vaporizer cartridge in the cartridge receptacle are possible, in some vaporizers the shape of the vaporizer cartridge, or at least a shape of the end of the vaporizer cartridge that is configured for insertion into the cartridge receptacle may have rotational symmetry of at least order two. In other words, the vaporizer cartridge or at least the insertable end of the vaporizer cartridge may be symmetric upon a rotation of 180° around an axis along which the vaporizer cartridge is inserted into the cartridge receptacle. In such a configuration, the circuitry of the vaporizer may support identical operation regardless of which symmetrical orientation of the vaporizer cartridge occurs.

In some examples, the vaporizer cartridge, or at least an end of the vaporizer cartridge configured for insertion in the cartridge receptacle may have a non-circular cross section transverse to the axis along which the vaporizer cartridge is inserted into the cartridge receptacle. For example, the non-circular cross section may be approximately rectangular, approximately elliptical (e.g., have an approximately oval shape), non-rectangular but with two sets of parallel or approximately parallel opposing sides (e.g., having a parallelogram-like shape), or other shapes having rotational symmetry of at least order two. In this context, approximately having a shape indicates that a basic likeness to the described shape is apparent, but that sides of the shape in question need not be completely linear and vertices need not be completely sharp. Rounding of both or either of edges or vertices of the cross-sectional shape is contemplated in the description of any non-circular cross section referred to herein.

The at least two cartridge contacts and the at least two receptacle contacts can take various forms. For example, one or both sets of contacts may include conductive pins, tabs, posts, receiving holes for pins or posts, or the like. Some types of contacts may include springs or other urging features to cause better physical and electrical contact between the contacts on the vaporizer cartridge and the vaporizer body. The electrical contacts may optionally be gold-plated, and/or can include other materials.

Figure 1B:
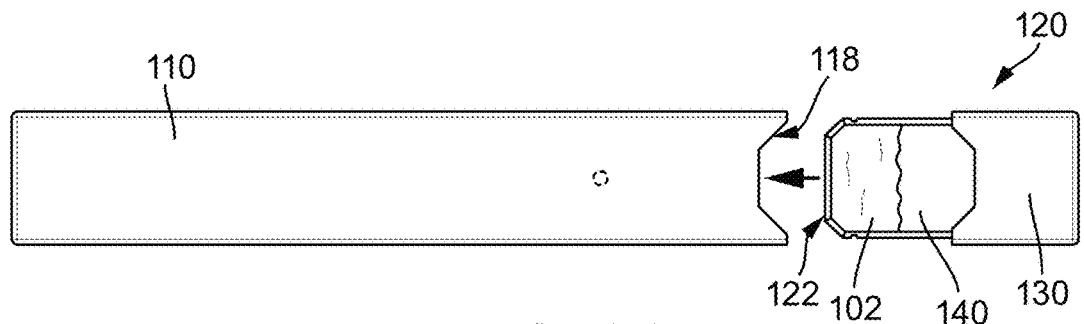
FIG. 1B illustrates a top view of an embodiment of the vaporizer device of FIG. 1A showing a vaporizer cartridge separated from a vaporizer device body.

FIG. 1B illustrates an embodiment of the vaporizer body 110 having a cartridge receptacle 118 into which the vaporizer cartridge 120 may be releasably inserted. FIG. 1B shows a top view of the vaporizer 100 illustrating the cartridge being positioned for insertion into the vaporizer body 110. When a user puffs on the vaporizer 100, air may pass between an outer surface of the vaporizer cartridge 120 and an inner surface of a cartridge receptacle 118 on the vaporizer body 110. Air can then be drawn into an insertable end 122 of the cartridge, through the vaporization chamber that includes or contains the heating element and wick, and out through an outlet of the mouthpiece 130 for delivery of the inhalable aerosol to a user. The reservoir 140 of the vaporizer cartridge 120 may be formed in whole or in part from translucent material such that a level of vaporizable material 102 is visible along the vaporizer cartridge 120.

Figure 2:
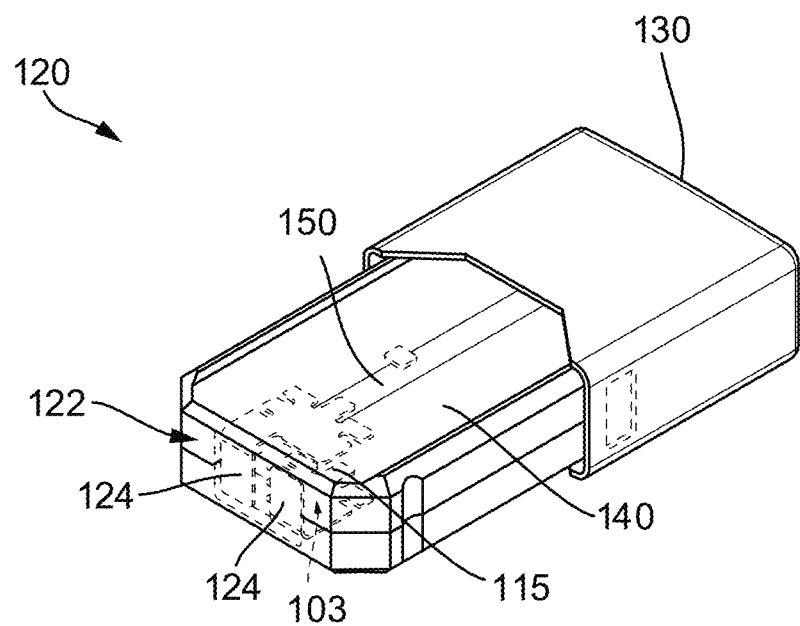
FIG. 2 illustrates a top perspective view of a vaporizer cartridge.

FIG. 2 illustrates an embodiment of a vaporizer cartridge 120 including a wick 103 (e.g., a thermal wick or a hollow wick) consistent with implementations of the current subject matter. The vaporizer cartridge 120 includes a reservoir 140 configured to hold a vaporizable material and a proximal mouthpiece 130. The vaporizer cartridge 120 may also include cartridge contacts 124 at a distal end that is configured to mate with a conductive connector of a power source, such as a body of a vaporizer device to which the vaporizer cartridge 120 may couple thereto. The vaporizer cartridge 120 may also include a resistive heating element 115 (such as atomizer 141, shown in FIG. 1A) adjacent the wick 103. The heating element 115 may be conductively connected to cartridge contacts 124. As shown in FIG. 2, an air path 150 may extend through the reservoir 140.

Figure 3:
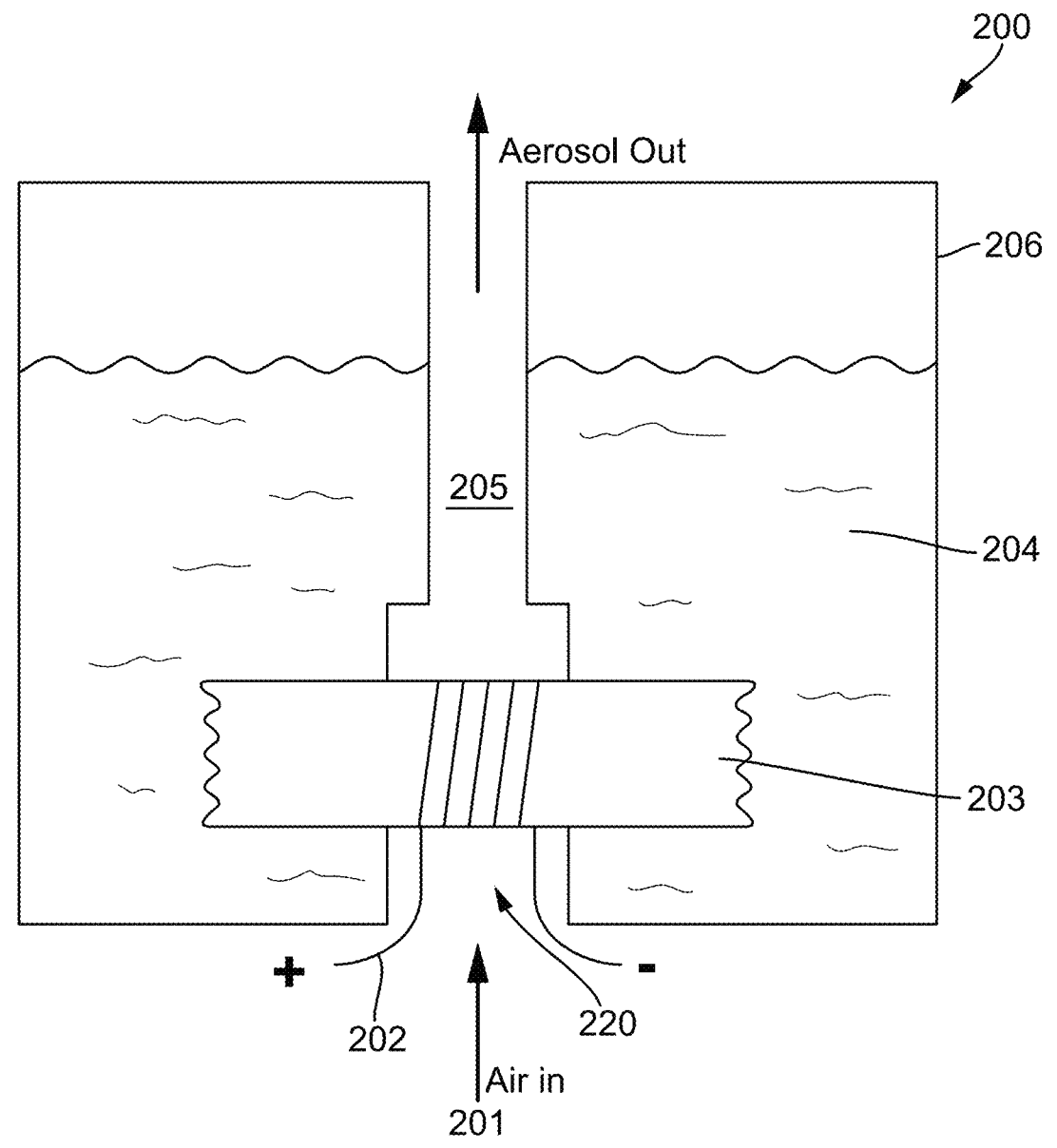

FIG. 3 illustrates a schematic representation of a vaporizer cartridge 200 in which a wick 203, consistent with implementations of the current subject matter, may be incorporated, such as either the hollow or thermal wicks described herein. The vaporizer cartridge 200 includes a reservoir 206 for holding a vaporizable material 204 such as a liquid, gel, solid, semi-solid, or wax vaporizable material including but not limited to nicotine oil, cannabis oil, glycerol, vegetable glycerin, glycol, propylene glycol, water, flavorants, additives, and/or the like. The vaporizable material 204 may include one or more active agents, including nicotine, cannabinoids, terpenes, or any combinations thereof.

As shown in FIG. 3, the reservoir 206 can include two chambers that are in fluid communication with each other, however, they can be separated (e.g., holding different vaporizable materials). An air path 205 extends through the vaporizer cartridge 200 such that air may be drawn in from the bottom or base of the vaporizer cartridge 200 at an air inlet 201 and pulled over and/or around a heating element 202 and the wick 203. In some implementations, the heating element 202 (e.g., a resistive heating coil) may be wrapped around and/or embedded within the wick 203. Additionally, the vaporizer cartridge 200 may include a vaporization chamber 220 that includes the wick 203 and heating element 202. For example, the vaporization chamber 220 is a chamber through which the airflow passes and the vaporizable material 204 is vaporized.

The wick 203 may include at least one porous material that draws the vaporizable material 204 from the reservoir 206 to the vaporization chamber 220. For example, when a user puffs on a mouthpiece of the vaporizer cartridge 200, air may flow into the air inlet 201. Simultaneously or nearly simultaneously, the heating element 202 may be activated (e.g., by a pressure sensor, pushbutton, etc.) thereby vaporizing the vaporizable material saturating the wick 203. The incoming air may flow through the vaporization chamber 220, including over the wick 203 and/or heating element 202, and collect the vaporized vaporizable material. The vaporized material may be condensed and inhaled as an aerosol via the air path 205.

Various embodiments of the wick, such as various embodiments of a thermal wick and hollow wick, are disclosed in greater detail below. Embodiments of the thermal wick and hollow wick can be implemented in a variety of cartridges, including vaporizer cartridge 120 and vaporizer cartridge 200 for improving the efficiency and effectiveness of vaporizing one or more vaporizable materials with a vaporizer.

Figure 4:
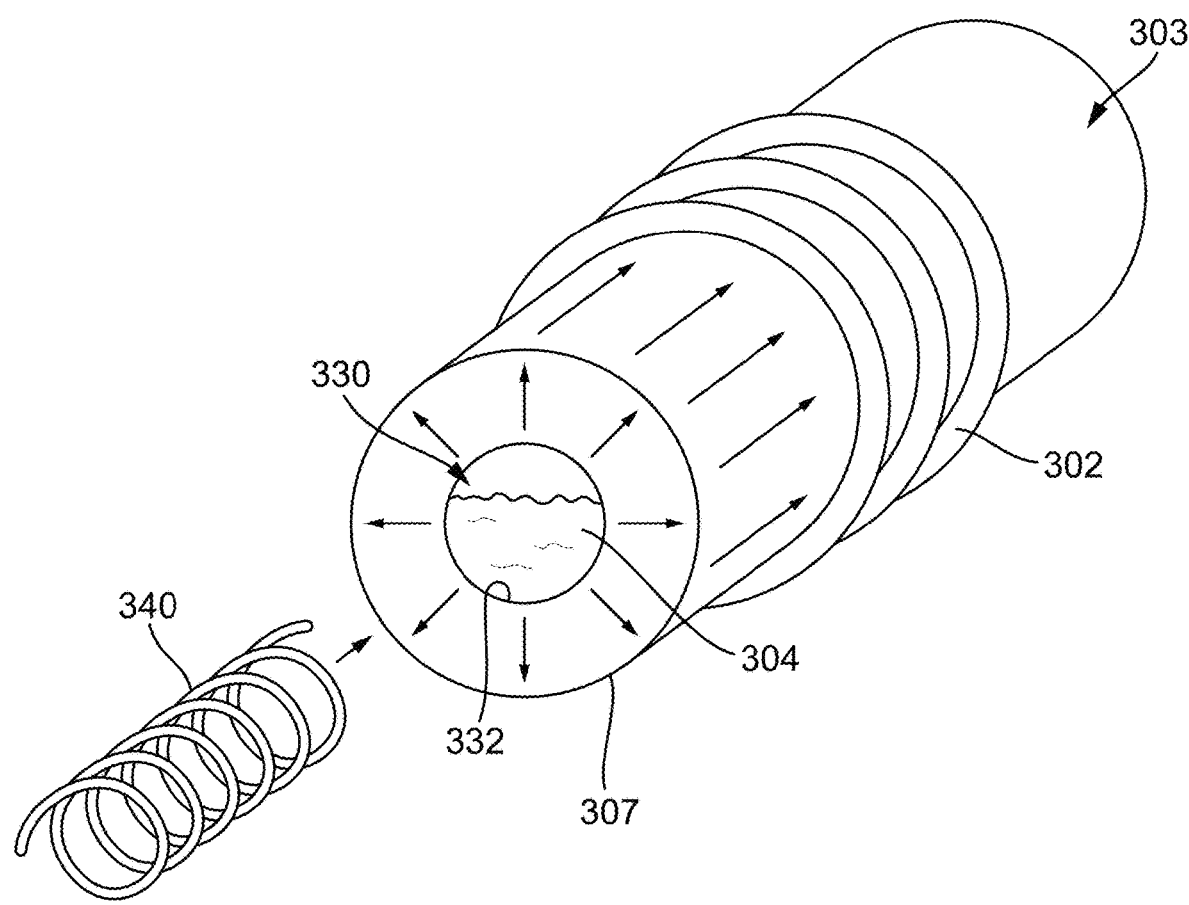
FIG. 4 illustrates an end perspective view of an embodiment of a wick including a hollow core.

FIG. 4 illustrates an embodiment of a hollow wick 303 that may be incorporated in any of the cartridges and/or vaporizer devices disclosed herein. As shown in FIG. 4, the hollow wick 303 includes an outer porous jacket 307 that at least partly surrounds a hollow core or fluid passageway 330. The hollow wick 303 may be positioned adjacent a heating element, such as a coiled heating element 302 that may be wound around a length of the hollow wick 303.

The outer porous jacket 307 can be formed out of a variety of materials, such as fibrous braided or woven high temperature resistant material (e.g., silica, cotton, etc.), that may have a high porosity. Such high porosity of the outer porous jacket 307 allows the outer porous jacket 307 to draw vaporizable material axially along the length of the hollow wick 303, such as from the reservoir to near or adjacent to the heating element for vaporization in the vaporization chamber.

As shown in FIG. 4, an inner wall 332 of the outer porous jacket 307 forms the fluid passageway 330. The fluid passageway 330 of the hollow wick 303 is open and void of material comprising the hollow wick 303. Additionally, one or both opposing ends of the hollow wick 303 may be open thereby allowing vaporizable fluid 304 contained in the reservoir to flow into the fluid passageway 330, as shown in FIG. 4. Once in the fluid passageway 330, the vaporizable fluid 304 can be absorbed through the inner wall 332 and radially through the outer porous jacket 307 towards the heating element 302 or outer surface of the hollow wick 303. As such, the hollow wick 303 enables both axial capillary action and radial capillary action (e.g., orthogonal to axial capillary action) of the vaporizable fluid 304. This increases the rate and volume of vaporizable fluid 304 that can be vaporized in the vaporization chamber. For example, a shorter distance is required for vaporizable fluid 304 to travel radially from the fluid passageway 330 to the heating element 302 (or sufficiently close thereto) for becoming vaporized in the vaporization chamber compared to vaporizable fluid 304 that travels axially from one or both ends of the hollow wick 303 to the heating element 302 (or sufficiently close thereto) for becoming vaporized. As discussed above, such as with respect to FIG. 3, the cartridge can be configured such that both ends of the hollow wick 303 are in contact with vaporizable fluid contained in the reservoir of the cartridge.

As shown in FIG. 4, the hollow wick 303 is cylindrical in shape, however, the hollow wick 303 may include a variety of shapes and sizes without departing from the scope of this disclosure. For example, the hollow wick 303 can include a square, rectangular, elliptical, triangular, or other shaped cross-section. Furthermore, the fluid passageway 330 may have the same, similar, or different cross-sectional shape as the outer diameter of the hollow wick 303.

In some embodiments, the hollow wick 303 includes an internal support, such as the internal support 340 illustrated in FIG. 4 that assists with retaining the shape of the fluid passageway 330. For example, the internal support 340 includes an elongated helical coil or spring having a circular cross-section and an outer diameter that is configured to mate against the inner wall 332 of the fluid passageway 330 thereby assisting with retaining a cylindrical shape of the fluid passageway 330. The internal support 340 can include any number of shapes and configurations and can be made of a variety of materials (such as a metal or plastic material) without departing from the scope of this disclosure.

The hollow wick 303 can provide a variety of benefits, including allowing the hollow wick 303 to have a smaller outer diameter while still achieving improved and/or desired effects associated with effective and efficient vaporization, as discussed herein. Additionally, the hollow wick 303 provides improved permeability (fluid flow) by allowing the vaporizable fluid 304 to flow through the hollow wick 303 (via the fluid passageway 330), thereby allowing absorption of the vaporizable fluid 304 both in the radial and axial directions along the hollow wick 303. Thermal benefits of the hollow wick 303 may include conductive losses to the vaporizable fluid that cause a change in the vaporizable fluid properties (e.g., viscosity, surface tension, etc.). Other benefits are within the scope of this disclosure.

Figure 5:
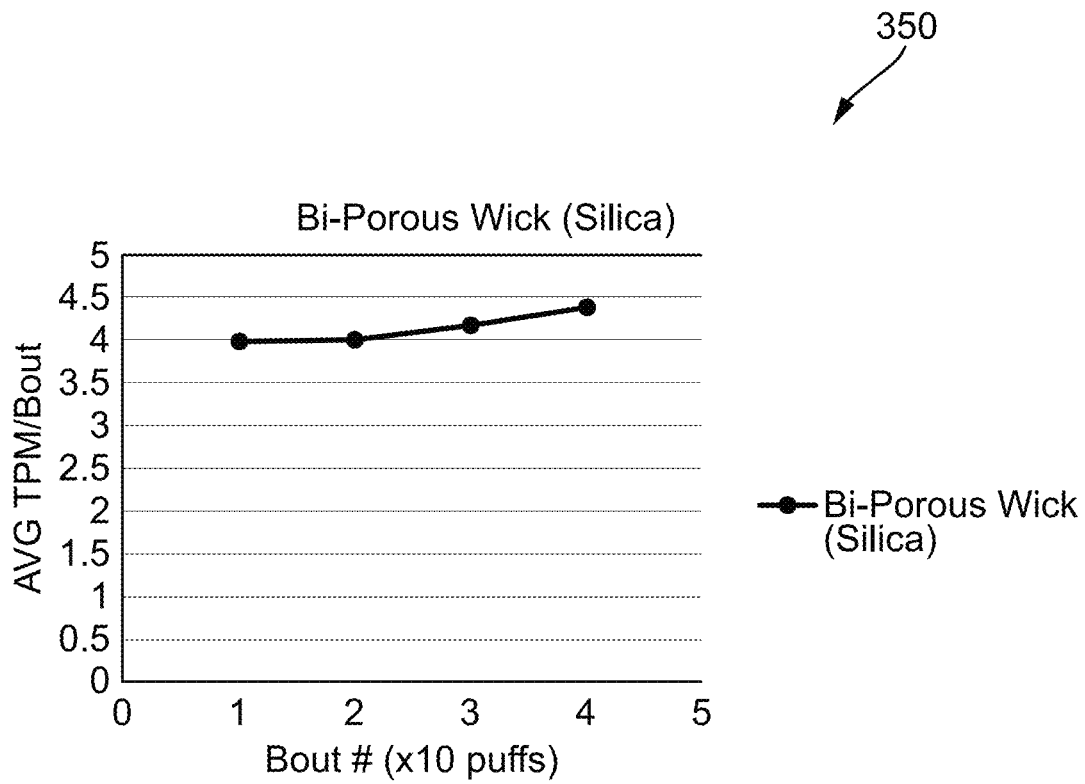
FIG. 5 illustrates a graph showing a total particulate mass (TPM) of vaporizable material that may be vaporized using an embodiment of a wick having a hollow core.

FIG. 5 illustrates a graph 350 showing an example total particulate mass (TPM) of vaporizable material vaporized with a hollow wick consistent with various implementations of the current subject matter. As illustrated in FIG. 5, the average TPM per puff can increase with successive puffs, thereby illustrating a potential benefit of the hollow wick, which is to efficiently and effectively draw vaporizable fluid toward the heating element for becoming vaporized, including after successive puffs from the vaporizer.

Figure 6:
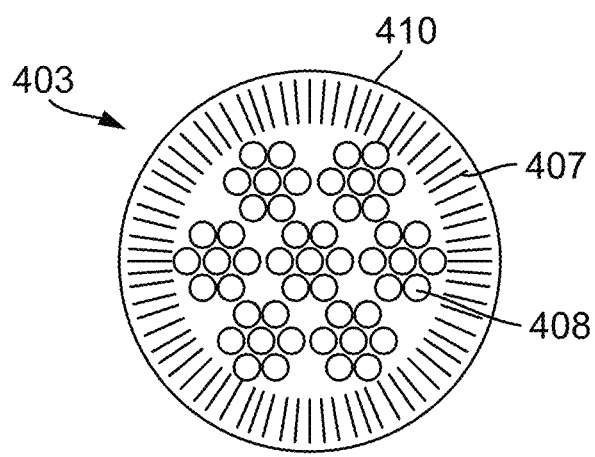
FIG. 6 illustrates a cross-sectional view of a first embodiment of a wick including a thermal core.

FIG. 6 illustrates a first embodiment of a thermal wick 403 that includes an outer porous jacket 407 and a thermally conductive core 408. The outer porous jacket 407 may include a bundle of fibers, such as silica fibers. The thermally conductive core 408 forms a central core region of the thermal wick 403. The outer porous jacket 407 surrounds or substantially surrounds the thermally conductive core 408. In some implementations, a separate sleeve 410 made of a porous wicking material may surround the silica fibers making up the outer porous jacket 407.

In some implementations, an axial thermal conductivity of the outer porous jacket is ~1.4 W/mK. The thermally conductive core 408 may be made of, for example, a stainless steel material, such as a stainless steel rope made from multiple twisted bundles of wire each containing individual strands of wire. In an example implementation, the wires of the stainless steel rope are each approximately 0.15 mm diameter/strand, and the overall rope diameter is approximately 1.5 mm. In an example implementation, the overall outside diameter of the thermal wick 403 may be approximately 2 mm, although other diameters may be used, including, for example, 0.5 mm to 5 mm diameters.

For example, as shown in FIG. 6, the thermally conductive core 408 of the thermal wick 403 includes stainless steel fibers. This may increase the void volume along the thermally conductive core 408 and also increase the thermal conductivity of the thermally conductive core 408. For example, in some embodiments the thermal conductivity may be approximately 15 W/mK, such as when the thermally conductive core includes nichrome fibers. In some embodiments, the thermal conductivity may be approximately 50 W/mK to approximately 60 W/mK, such as when the thermally conductive core includes stainless steel fibers. The outer porous jacket 407 in this example may serve more than one purpose. For example, the less thermally conductive outer porous jacket 407 (e.g., a braided silica sleeve) may radially surround the thermally conductive core 408 to electrically isolate and protect the heating coil, which may be wrapped around the thermal wick 403, from shorting on the thermally conductive core 408. The outer porous jacket 407 may also provide a capillary path to mitigate leakage through and around the thermally conductive core 408.

As shown in FIG. 6, the thermally conductive core 408 may be exposed at the ends to aid in the heating of the vaporizable material contained in the adjacent reservoir.

Although a thermally conductive material of the thermal wick 403 is typically electrically isolated from the heating element (e.g., heating element 115) by an outer porous jacket having a lower thermal conductivity, when power is applied to the heating element to vaporize the vaporizable material, the thermal wick 403 is heated by conduction and/or convection. The thermal wick 403 may be heated to a temperature that is below a vaporization temperature of the vaporizable material. In some variations, the thermal wick 403 is passively heated by the heating element. In some variations, the thermal wick 403 may be heated separately or additionally from the heating element, and may be, for example, heated by a separate heater. A separate (typically lower-temperature/warming) heater, which is also referred to herein as a wick heater, may therefore be thermally connected to the thermally conductive portion(s) of the thermal wick 403, and this separate heater may be driven from a separate heating circuit from the heating/vaporizing heating coil. Alternatively, the wick heater (warming heater) may be driven from the same control circuit of the heating coil (or, for example, connected in series or parallel to the control circuit and/or the heating coil). Thus, in some variations, the thermal wick 403 may be heated while the device is "on", even when the heating coil of the vaporizer/atomizer is not active.

The thermally conductive material may be a resistive heating material and/or a material having a high thermal conductivity. In other words, the thermally conductive material may have a thermal conductance that is greater than that of the porous wicking material. For example, the thermal conductance of the thermally conductive material may be at least about 5% greater than that of the porous wicking material. The thermal conductance of the thermally conductive material may be greater than that of the porous wicking material by approximately 3-9 W/mK. The thermal conductivity at or near room temperature of the thermally conductive material in the thermal wick may be greater than, for example, 5×, 10×, 15×, and/or 20× the thermal conductivity of standard wicking materials, such as cotton, silica, etc. Other thresholds may be established for characterizing a material as a high thermal conductivity material. Examples of the thermally conductive materials include but are not limited to copper (which has a high thermal conductivity of approximately 385 W/mK), steel, stainless steel, aluminum, titanium, nickel, or any metal/metal combination. In some implementations, the thermally conductive material is non-reactive with the vaporizable material. In some implementations in which the thermally conductive material is a reactive material, a coating or plating (e.g., an inert plating) may also be incorporated.

One or more materials of the thermal wick may have an increased thermal conductivity compared to silica or cotton wicks used in currently available vaporizers, and may optionally be electrically conductive. For example, in one variation, the thermal wick may include a ceramic material (or other porous material) that is formed in the shape of a tube or cylinder with thermally conductive particles (e.g., copper flakes or pieces) embedded or dispersed throughout.

An outer porous jacket of either the thermal wick or the hollow wick 303 may be made from any braided, stranded, or amorphous material which is not electrically conductive and which is stable at vaporization temperatures. The outer porous jacket may be formed of or include silica, cotton, glass (e.g., glass fibers), fiberglass, ceramic, or another porous material. In some implementations, the outer porous jacket can be a perforated material or tube. The outer porous jacket may be characterized as having a low thermal conductivity. For example, materials with a thermal conductivity less than 3 W/mK (e.g., at or near 25° C.) may be referred to as low thermal conductivity materials. Other thresholds may be established for characterizing a material as a low thermal conductivity material. For example, in one implementation the porous wicking material can include a bundle of approximately 17,000 silica fibers, each approximately with a 0.009 mm diameter, with the bundle constrained to a diameter of ~2 mm and cut to a length of approximately 10 mm.

Some embodiments of the wick consistent with implementations of the current subject matter include at least one feature associated with the hollow wick 303 and the thermal wick 403. For example, the internal support 340 of the hollow wick 303 illustrated in FIG. 4 can be made of a thermally conductive material. This can allow the internal support 340 to provide features and effects similar to the thermally conductive core 408 of the thermal wick 403.

Figure 7A:
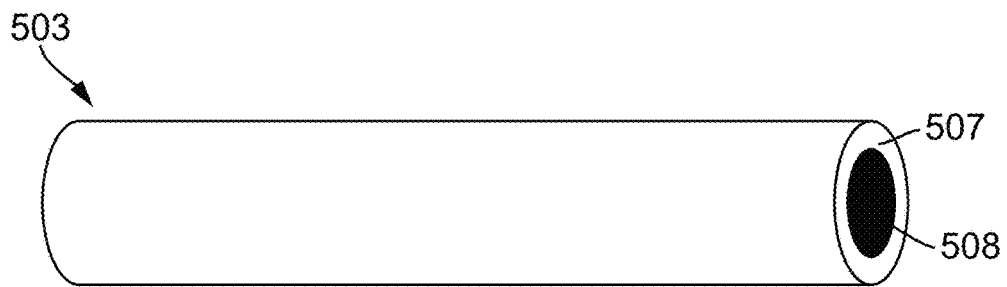
FIG. 7A illustrates a side view of a second embodiment of a wick including a thermal core.
Figure 7B:
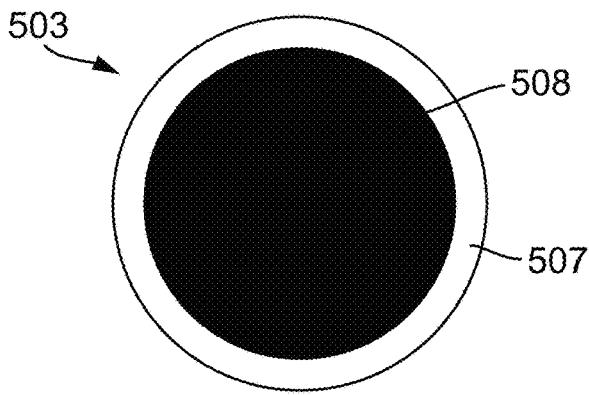
FIG. 7B illustrates an end view of the wick of FIG. 7A.

FIGS. 7A and 7B illustrate another embodiment of a thermal wick 503 including a thermally conductive core 508 extending the length of the thermal wick 503. The thermally conductive core 508 is radially surrounded by an outer porous jacket 507 having a lower thermal conductivity. The ends of the thermally conductive core 508 may be exposed, as shown in FIGS. 7A and 7B. As shown in FIG. 7B, the thermally conductive core 508 may be solid and/or not include fluid or air passageways.

Figure 8A:
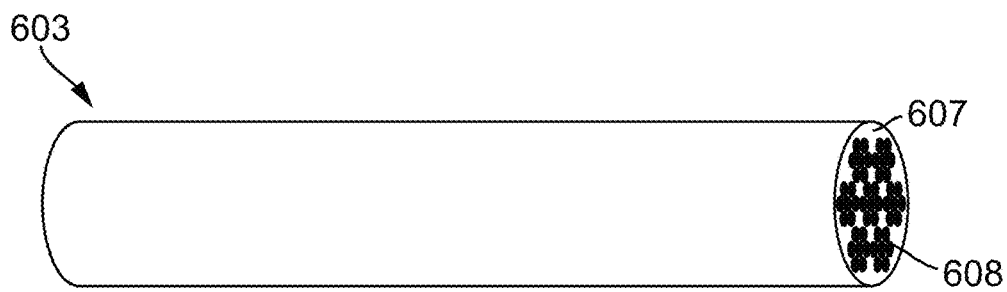
FIG. 8A illustrates a side view of a third embodiment of a wick including a thermal core.
Figure 8B:
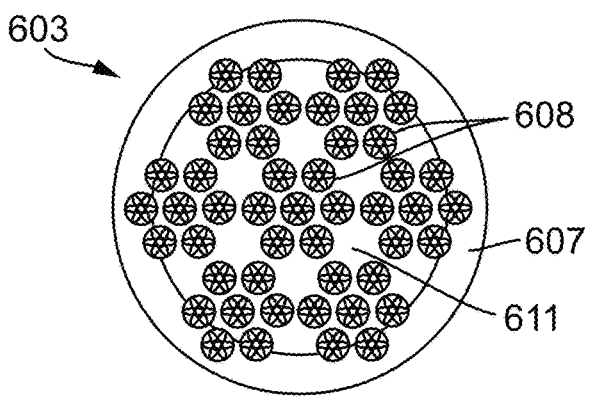
FIG. 8B illustrates an end view of the wick of FIG. 8A.

FIGS. 8A and 8B illustrate another embodiment of a thermal wick 603 including an inner core region made up of thermally conductive components or strands 608 and gaps or voids 611 positioned between the thermally conductive strands 608. For example, the gaps or voids 611 may be air or fluid gaps. An outer porous jacket 607 surrounds the inner core region of thermally conductive strands 608 and voids 611.

Figure 9A:
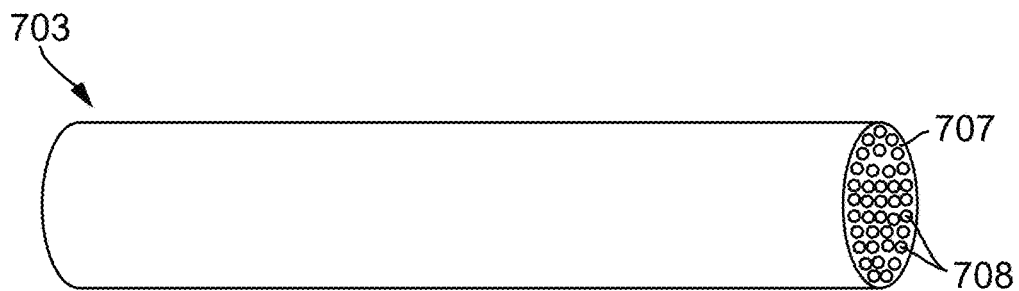
FIG. 9A illustrates a side view of a fourth embodiment of a wick including a thermal core.
Figure 9B:
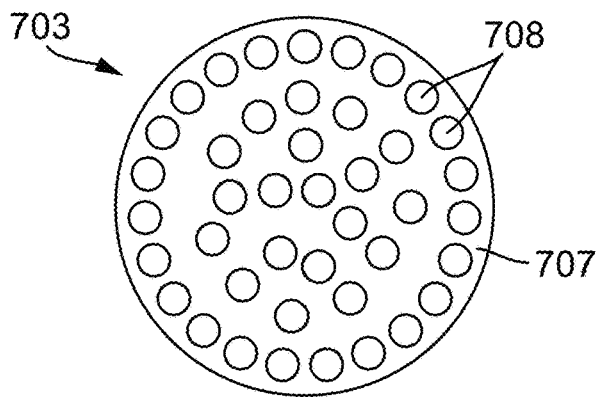
FIG. 9B illustrates an end view of the wick of FIG. 9A.

FIGS. 9A and 9B illustrate another embodiment of a thermal wick 703 including a conductive core 708 with a high thermal conductivity material (e.g., wires, braids, fibers, etc., of stainless steel, for example). The conductive core 708 extends along the length of the thermal wick 703 and is surrounded by an outer porous jacket 707 that has a lower thermal conductivity and is electrically conductive. As shown in FIGS. 9A and 9B, the high thermal conductivity material may be evenly or near evenly distributed through the volume of the thermal wick 703. The thermal wick 703 may also include internal void or gap regions (e.g., around the high thermal conductivity material). The individual strands of high thermal conductivity material (as shown in the sectional/end view of FIG. 7B and at the end of FIG. 7A) may be woven, braided, or otherwise in thermal contact with each other at various points along the length of the thermal wick 703.

Figure 10A:
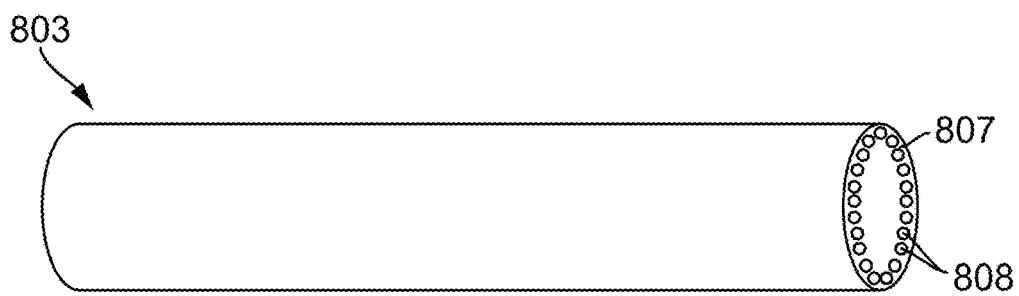
FIG. 10A illustrates a side view of a fifth embodiment of a wick including a thermal core.
Figure 10B:
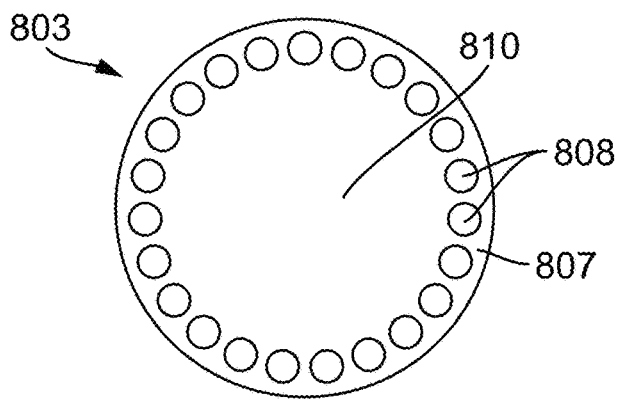
FIG. 10B illustrates an end view of the wick of FIG. 10A.

FIGS. 10A and 10B illustrate another embodiment of a thermal wick 803 including a plurality of high thermal conductivity strands 808 arranged along an inner peripheral region that is covered by an outer porous jacket 807 having lower thermal conductivity properties. In this example, the central region or core 810 may be the same material as the outer porous jacket, providing a larger cross-sectional area for wicking.

Any of the thermally conductive material may be formed into a filament, rope, bundle, chain, weave, braid, or the like, and may generally extend along all or a majority of the length of the thermal wick. The ends of the thermal wick may be open (e.g., exposing the high thermally conductive material to the vaporizable material in the reservoir), or they may be covered by the outer wicking material (e.g., low thermal conductivity material or insulating material) or by another material.

Figure 11A:
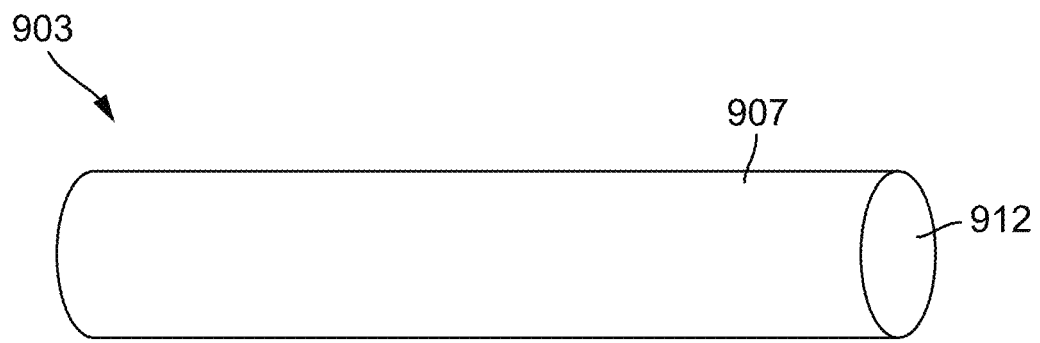
FIG. 11A illustrates a side view of a sixth embodiment of a wick including a thermal core.
Figure 11B:
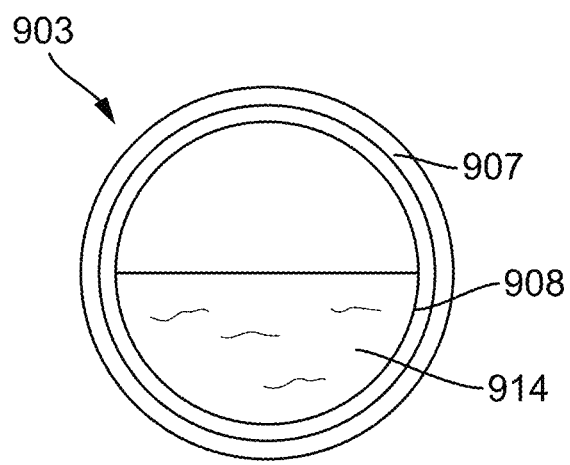
FIG. 11B illustrates an end view of the wick of FIG. 11A.

FIGS. 11A and 11B illustrate another embodiment of a thermal wick 903 including a thermally conductive core 908 surrounded by an outer porous jacket 907. The thermally conductive core 908 is a chamber containing a fluid 914, such as water. The ends of the thermal wick 903 are sealed with end caps 912 to contain the fluid 914 within the thermally conductive core 908. The end caps 912 may be formed of the same material as the thermally conductive core 908. This configuration results in significant heat transfer improvements and has a low thermal mass due to the configuration of the thermally conductive core 908.

In any of the thermal wick embodiments described herein, additional strands or lengths of high thermally conductive materials may extend through the length of the thermal wick. As mentioned, any of the thermal wick embodiments may include a plurality of voids/air gaps within the volume of the thermal wick. For example, the volume may include 2%-25% of voids/air gaps. These voids/air gaps may be near or adjacent to the high thermal conductivity material.

In general, the wicks described herein may be any appropriate diameter and length. For example, the thermal wick may have a diameter of approximately 0.5 mm-10 mm and a length of between approximately 0.5 mm and 30 mm.

In accordance with additional aspects of the current subject matter, a thermal wick may have a core containing between approximately 1 and 10,000 strands in a variety of orientations. The strand diameters may range from, for example, approximately 0.005 mm to 9.000 mm. The thermal core may also be a tube, or tubes, e.g., of approximately 0.25-9.25 mm outside diameter with a length of approximately 0.5-30 mm. The tube(s) may also have radial holes or slots to facilitate fluid transfer out of or between the tube(s). The thermal core may also be made of standard wicking fibers, such as silica, which are co-woven with some fraction of metallic fibers of a similar diameter. Metallic fiber fractions may range from 1-99%. The outer 0.25 mm, for example, of this core may be made of non-conductive (e.g., non-metallic) wicking material, including fibers, to prevent the heating coil from shorting.

Figure 12:
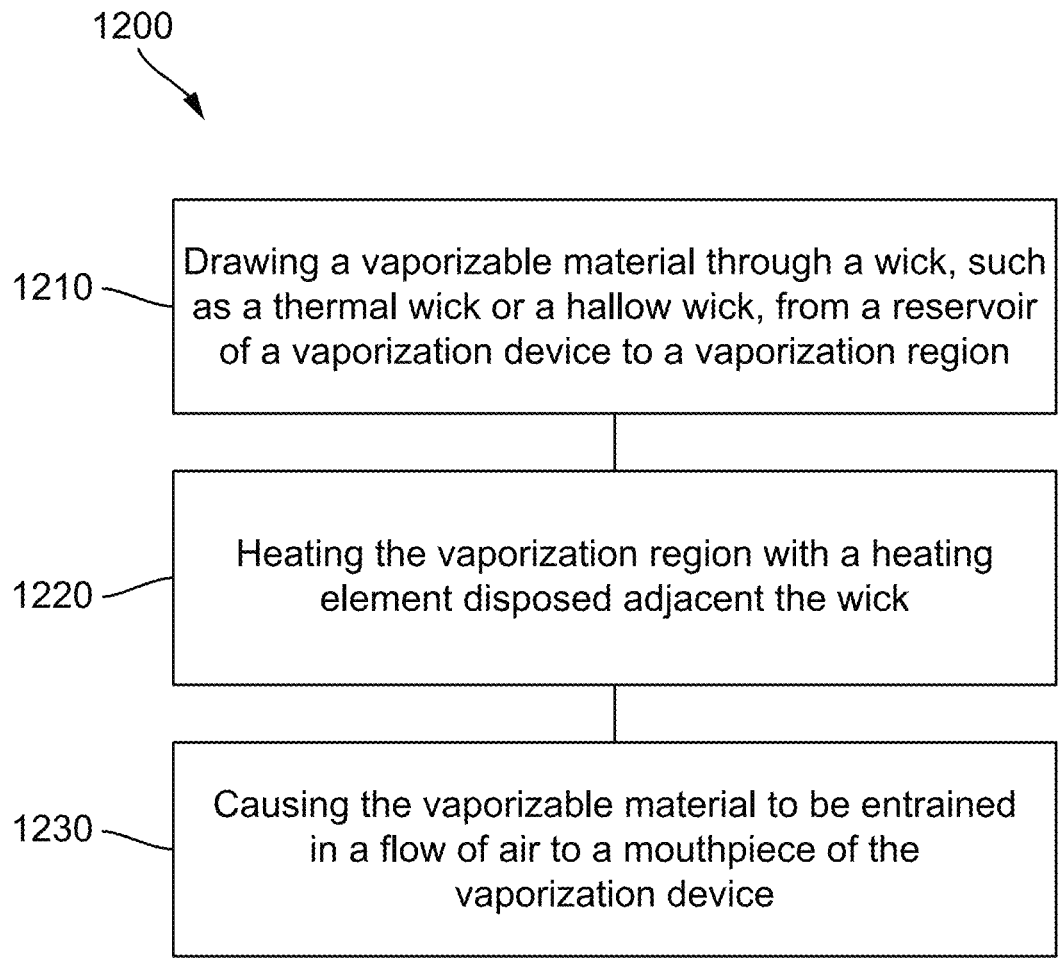
FIG. 12 shows a process flow diagram illustrating aspects of a method having one or more features consistent with implementations of the current subject matter.

FIG. 12 shows a process flow diagram 1200 illustrating aspects of a method having one or more features consistent with implementations of the current subject matter. At 1210, a vaporizable material is drawn, through a wick, from a reservoir of a vaporization device to a vaporization region. The wick can include any of the hollow wick or thermal wick embodiments disclosed herein. At 1220, the vaporization region is heated with a heating element disposed adjacent the wick and near or within the vaporization chamber. The heating causes vaporization of the vaporizable material in the vaporization chamber. At 1230, the vaporized vaporizable material is entrained in a flow of air directed to a mouthpiece of the vaporization device for inhalation by a user.

Terminology

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A cartridge for use with a vaporization device, the cartridge comprising:
    a reservoir configured to contain a vaporizable material;
    a wick configured to draw the vaporizable material from the reservoir to a vaporization region, the wick including a porous wicking material surrounding at least a part of a hollow core, the porous wicking material allowing a radially directed absorption of the vaporizable material from the hollow core towards an outer surface of the wick, the porous wicking material further allowing an axially directed absorption of the vaporizable material along a length of the wick; and
    a heating element disposed within the vaporization region and adjacent the wick, the heating element configured to heat the vaporizable material drawn from the reservoir.

2. The cartridge of claim 1, wherein the hollow core is in fluid communication with the reservoir.

3. The cartridge of claim 1, wherein the hollow core extends between opposing ends of the wick.

4. The cartridge of claim 3, wherein the opposing ends of the wick each include an opening that allows the vaporizable material to flow into the hollow core.

5. The cartridge of claim 1, wherein the wick further includes a support structure that is separate from the heating element, the support structure configured to retain a shape of the hollow core.

6. The cartridge of claim 5, wherein the support structure includes a spring having a helical shape.

7. The cartridge of claim 5, wherein the shape of the hollow core includes a cylindrical shape.

8. The cartridge of claim 1, wherein the hollow core is void of material.

9. The cartridge of claim 1, wherein the hollow core comprises a thermally conductive material extending therethrough.

10. The cartridge of claim 9, wherein the thermally conductive material comprises one or more of copper, steel, stainless steel, aluminum, titanium, nickel, or any metal.

11. The cartridge of claim 1, wherein the porous wicking material comprises one or more of fibrous braided or woven high temperature resistant material, silica, cotton, or other material having a high porosity.

12. The cartridge of claim 1, wherein the vaporizable material is a liquid.

13. The cartridge of claim 1, wherein the heating element is a coil that wraps around a circumference of the wick.

14. The cartridge of claim 1, wherein the heating element is in thermal communication with the wick thereby allowing the heating element to increase a temperature of at least the porous wicking material.

15. The cartridge of claim 1, wherein the radially directed absorption is orthogonal to the axially directed absorption.

16. A wick for including in a cartridge for use in a vaporization device, the wick comprising:
    a porous wicking material surrounding at least a portion of a hollow core, the porous wicking material allowing a radially directed absorption of a vaporizable material from the hollow core towards an outer surface of the wick, the porous wicking material further allowing an axially directed absorption of the vaporizable material along a length of the wick; and
    a support structure configured to retain a shape of the hollow core, the support structure including a spring having a helical shape.

17. The wick of claim 16, wherein the hollow core extends between opposing ends of the wick.

18. The wick of claim 17, wherein the opposing ends of the wick each include an opening that allows a vaporizable material to flow into the hollow core.

19. The wick of claim 16, wherein the shape of the hollow core includes a cylindrical shape.

20. The wick of claim 16, wherein the radially directed absorption of a vaporizable material is orthogonal to the axially directed absorption of the vaporizable material.

21. The wick of claim 20, wherein the vaporizable material is a liquid.

22. The wick of claim 16, wherein the hollow core is void of material.

23. The wick of claim 16, wherein the hollow core comprises a thermally conductive material extending therethrough.

24. The wick of claim 16, further comprising a heating element coupled to at least one side of the wick.

25. The wick of claim 24, wherein the heating element is a coil that wraps around a circumference the wick.

26. A method comprising:
    drawing a vaporizable material into a porous wicking material of a wick in a first direction, the porous wicking material surrounding at least a portion of a hollow core, the wick further comprising:
        a support structure that is separate from a heating element, the support structure configured to retain a shape of the hollow core, the support structure including a spring having a helical shape; and
    drawing the vaporizable material into the porous wicking material of the wick in a second direction, wherein the second direction is orthogonal to the first direction and extends between the hollow core and an outer surface of the porous wicking material.

27. The method of claim 26, wherein the first direction extends parallel to a longitudinal axis of the wick.

28. The method of claim 26, further comprising transferring heat along a thermally conductive material extending along the hollow core.

* * * * *